United States Patent [19]

Sederoff et al.

[11] Patent Number: 4,886,937

[45] Date of Patent: Dec. 12, 1989

[54] METHOD FOR TRANSFORMING PINE

[75] Inventors: Ronald R. Sederoff, Albany, Calif.; Anne-Marie Stomp, Wendell, N.C.; Larry W. Moore, Corvallis, Oreg.; Scott W. Chilton, Raleigh, N.C.

[73] Assignee: North Carolina State University, Raleigh, N.C.

[21] Appl. No.: 211,149

[22] Filed: Jun. 22, 1988

Related U.S. Application Data

[63] Continuation of Ser. No. 735,669, May 20, 1985, abandoned.

[51] Int. Cl.$^4$ .................... A01H 1/04; C12N 15/00
[52] U.S. Cl. ................... 800/1; 435/172.3; 935/56; 935/67
[58] Field of Search ............. 435/172.3, 320, 252.2; 800/1

[56] References Cited

U.S. PATENT DOCUMENTS

4,459,355 7/1984 Cello et al. ................. 435/172.3
4,693,976 9/1987 Schilperoort et al. ............ 435/172.3

OTHER PUBLICATIONS

Smith, C. O., *J. Agricult. Res.* 59, 919 (1939).
Smith, C. O., *Phytopathology* 32, 1005 (1942).
DeCleene, M. et al., *Bot. Rev.* 2, pp. 389–391, 414–417 (1976).
Anderson, A. R. et al., *Phytopathology* 69, 320 (1979).
Knauf, V. C. et al., *Phytopathology* 72, 1545 (1982).
Caplan, A. et al., *Science* 222, 815 (1983).
Hood, E. E. et al., *Bio/Technology* 2, 702 (1984).
Powledge, T. M., *Bio/Technology* 2, 763 (1984).
Horsch, R. B. et al., *Science* 227, 1229 (1985).
Aitken-Christie, J. et al., "Multiplication of Meristematic Tissue—A New Tissue Culture System for Radiata Pine", *Genetic Manipulation of Woody Plants* (J. Hanover and D. Keathley, eds.), Plenum Press (New York), 1987.
Matthysee, A. and Gurlitz, G., "Plant Cell Range for Attachment of *Agrobacterium tumefaciens* to Tissue Culture Cells", *Physiological Plant Pathology* 21, 381 (1982).
Farnum, P. et al., "Biotechnology of Forest Yield", *Biotechnology and Biological Frontiers*, 169 (P. Abelson, ed.), 1984.
Barton, K. and Brill, W., "Prospects in Plant Genetic Engineering", *Biotechnology and Biological Frontiers*, 121, 123 (p. Abelson, ed.).
Banthorpe, D. and Njar, V., *Phytochemistry* 23, 295 (1984).
Brown, C. and Sommer, H., *Tappi* 60, 72 (Jun. 1977).
Browne, F., "Pests and Diseases of Forest Plantation Trees", 1094–1115, 1127–1128 (Clarendon Press, Oxford, England, 1968).
Buchanan, M., Extraneous Components of Wood, in "The Chemistry of Wood", (B. L. Browning, ed. 1963) (Wiley Interscience, New York, N.Y.).
Cartwright, K. and Findley, W., "*Decay of Timber and its Prevention*", 266–270 (Her Majesty's Stationery Office, London, 1958).
Gladfelter, H. and Phillips, G., *Plant Cell Reports* 6, 163–166 (1987).
Kaul, K. and Kochhar, T., *Plant Cell Reports* 4, 180–183 (1985).
Kaul, K., *Plant Cell Reports* 6, 5–7 (1987).
Konar, R. and Singh, M., *Z. Pflanzenphysiol. Bd.* 99, 173–177 (1980).
Mansfield, J., *Biochemical Plant Pathology* 12, 237–241 (1983).
Reilly, K. and Brown, C. Georgia Forest Research Paper 86, 1–9, (Oct. 1976).
Wagley, L. et al., *Plant Cell Reports* 6, 167–171 (1987).

*Primary Examiner*—Charles F. Warren
*Assistant Examiner*—David T. Fox
*Attorney, Agent, or Firm*—Bell, Seltzer, Park & Gibson

[57] ABSTRACT

A method of transforming pine is disclosed wherein pine cells are inoculated with a strain of *Agrobacterium tumefaciens*. The strain contains a Ti plasmid which is capable of causing grown gall in the pine or a derivative of the Ti plasmid.

16 Claims, No Drawings

METHOD FOR TRANSFORMING PINE

This is a continuation of co-pending application Ser. No. 06/735,669, filed on May 20, 1985, now abandoned.

BACKGROUND OF THE INVENTION

1. Field of the Invention

The present invention relates to a method for transforming the genus Pinus with *Agrobacterium tumefaciens*. More particularly, the present invention relates to the transformation of Pinus species with strains of *A. tumefaciens* which harbor those Ti plasmids which are capable of causing crown gall in Pinus or derivatives thereof.

2. Description of the Prior Art

*A. tumefaciens* is a soil bacterium that causes crown gall on plants by infecting wounds that are generally below or at the soil surface; however, aerial plant parts can also be infected. A large tumor-inducting (Ti) plasmid is essential for tumor formation in the infected plant. A portion of the Ti plasmid, called TDNA, is transferred to the plant nuclear DNA where it is stably maintained and transcribed into mRNA. The TDNA codes for several functions which are expressed by the transformed plant cell. These functions include tumorigenesis, an effecting of hormone levels and bacterial metabolite (opine) synthesis.

The Ti plasmids are classified into two groups according to the number of host plants they can infect. A bacterial strain containing a wide host-range Ti plasmid can infect many dicotyledonous angiosperms as well as several gymnosperms. DeCleene, M. et al, *Botan. Rev.* 42, 389 (1976). However, each strain of *A. tumefaciens* has an overlapping but not necessarily identical host-range with other strains. This trait is primarily determined by the type of Ti plasmid present in the strain. Not all plants, including many dicotyledonous angiosperms and many gymnosperms, can be infected by *A. tumefaciens*.

Ti plasmids can be manipulated as gene vectors and have been used for the stable introduction and expression of foreign genes in plant cells and regenerated plants. See, for example, Fraley, R. T. et al, *Proc. Nat. Acad. Sci. USA* 84, 4803 (1983); Herrera-Estrella, L. et al. *EMBO J* 2, 987 (1983); Helmer, G. et al, *Bio/Technology* 2, 520 (1984); and Murai, N. et al, *Science* 222, 476 (1983). The key is to find a Ti plasmid which can infect the desired plant cell. This Ti plasmid can then be manipulated using standard techniques to enable the genetic engineering of the desired plant. The key element of the Ti plasmid is the vir region, which appears to be species-specific. In addition, TDNA, which does not appear to be species-specific, must be present to enable transfer of the desired DNA into the plant genome. These functions can be contained on separate plasmids within the transforming strain of *A. tumefaciens*.

The application of genetic engineering to conifers is in the initial stages. Included among the conifers are members of the family Pinaceae, including members of the genus Pinus. Very little information is presently available concerning the transformation of Pinaceae, especially Pinus, species. DeCleene, M., et al, supra, describe the infection of several members of the family Pinaceae by the *A. tumefaciens* strain B6. However, B6 was not able to infect any members of the genus Pinus. Prior to the present invention, no strain of *A. tumefaciens* was known to infect members of the genus Pinus.

U.S. Pat. No. 4,459,355 describes a method for transforming plant cells. The method involves the use of any *A. tumefaciens* which can transfer its Ti plasmid to the plant cell which is to be transformed. The patent indicates that the plant cell could come from a dicotyledon such as tobacco and tomato, or from a gymnosperm such as loblolly pine, cedar and Douglas fir. However, no transformation of loblolly pine is shown. The only example is directed to the transformation of tomato with the *A. tumefaciens* strain 15955. This strain is not capable of infecting pine. Furthermore, prior to the present invention, no strain of *A. tumefaciens* was known to infect pine, i.e., genus Pinus, even though strains were known to infect cedar and Douglas fir.

The present invention provides a method for transforming pine. Strains of *A. tumefaciens* have been identified which are capable of transforming pine. Additional strains can be identified by using the procedures described herein. All of these strains are useful for genetically engineering pine.

SUMMARY OF THE INVENTION

The present invention comprises a method for transforming a member of the genus Pinus. The method comprises inoculating cells of a species of Pinus with a strain of *A. tumefaciens* containing a Ti plasmid which is capable of causing crown gall in said species or a derivative of said Ti plasmid. Cells of a seedling, of a hypocotyl or of a leaf disc may be inoculated with the bacterium. Suitable strains include U3 and M2/73.

DETAILED DESCRIPTION OF THE INVENTION

The present invention is directed to a method for transforming pine, i.e., members of the genus Pinus. The method utilizes a strain of *A. tumefaciens* with which pine cells are inoculated to cause transformation of the pine cells. The strain of *A. tumefaciens* contains either a Ti plasmid which is capable of causing crown gall in said pine or a derivative of the Ti plasmid. As used herein, a derivative of the Ti plasmid refers to one or more plasmids which contain the vir region of the original Ti plasmid. The vir region is important for efficient transformation, and appears to be species-specific. The derivative must also contain at least a portion of TDNA to enable transfer of genetic material to the pine cells. It appears that any TDNA, such as from the original Ti plasmid or any other Ti plasmid, can be used for this purpose. The TDNA portion may be present on the same or a separate plasmid. In this manner, a single plasmid may contain both a vir region and TDNA portion, or alternatively, a vir region and the TDNA portion may be present on separate plasmids. The original Ti plasmid is one which causes crown gall on pine. An "appropriate" Ti plasmid or derivative is used herein to refer to one which is capable of causing crown gall in pine.

If desired, the original Ti plasmid can be modified to contain an inserted DNA sequence which contains one or more genes and preferably also their regulatory elements or other plant-recognizable regulatory elements. These genes may code for one or more proteins which can confer desired properties, such as disease resistance, salt tolerance, wood qualities, etc., to the transformed pine. The DNA sequence can be inserted into the Ti plasmid using techniques well known in the art. The insertion should not significantly interfere with the ability of the resulting Ti plasmid derivative (so called because it contains at least a portion of the TDNA) to be transferred from *A. tumefaciens* to a pine cell.

Alternatively, a Ti plasmid derivative can be prepared by inserting the desired DNA sequence into a derivative plasmid which contains only the borders of the TDNA, as is well known in the art. See Fraley, R. T. et al, supra, Henera-Estrella, L. et al, supra, Helmer, G. et al, supra, and Murai, N. et al, supra.

Any strain of *A. tumefaciens* may be used to transform pine as long as it carries the appropriate Ti plasmid or derivative. Any oncogenic strain of *A. tumerfaciens* can be used which can transfer its own appropriate Ti plasmid or derivative to the pine cell. If desired, a normally non-oncogenic strain of *A. tumefaciens* can be used which has been rendered oncogenic by receiving an appropriate Ti plasmid or derivative from another strain of *A. tumefaciens* or *Escherichia coli* through procedures well known in the art.

The method of transforming pine is not critical as long as the transfer of genetic material occurs. Suitable methods include many which are well known in the art. These include, but are not limited to, inoculating a wound site on a pine seedling with *A. tumefaciens*, inoculating pine cells with *A. tumefaciens* in the presence of the appropriate opine metabolite or precursor thereof, inoculating a culture of pine protoplasts with *A. tumefaciens* or spheroplasts of *A. tumefaciens*, and inoculating leaf discs with *A. tumefaciens*. Since individual cells of pine are transformed by each of these procedures, each procedure will be considered herein to involve the inoculation of pine cells with a strain of *A. tumefaciens*.

It is known that organogenesis can be induced from leaf parts of pine and other conifers. Consequently, transformed pine can be obtained by the leaf disc transformation procedure described by Horsch, R. B. et al, *Science* 227, 1229 (1985).

Pine which may be transformed by the method of the present invention include (but are not limited to) the following: *Pinus taeda* (loblolly pine), *P. lambertiana* (sugar pine), *P. ponderosa*, *P. radiata*, *P. elliottii* (slash pine), Afghan pine, *P. sylvestris*, *P. strobus*, *P. virginiana*, and other Christmas tree varieties.

Prior to the present invention, strains of *A. tumefaciens* capable of transforming pine were not known. Assay methods have been developed for identifying strains of *A. tumefaciens* which can transform pine. Utilizing the assay methods, strains U3 and M2/73 have been found to be capable of transforming pine. Other suitable strains of *A. tumefaciens* can be identified by performing the assay methods with any strain of *A. tumefaciens*. Any strain of *A. tumefaciens*, including U3 and M2/73, which has been identified by either of the assay methods is capable of transforming pine. The plasmids contained within these strains can be utilized as previously discussed. *A. tumefaciens* strain U3 has been deposited wth the ATCC and assigned number 53,124. *A. tumefaciens* strain M2/73 has also been deposited with the ATCC, and assigned number 53,125. These cultures were deposited on May 14, 1985.

The first assay method involves the inoculation of pine seedlings. Pine seedlings, generally five inches high for convenience, are inoculated in the apical region with a strain of *A. tumefaciens*. The inoculation can be accomplished by wounding the seedling in the apical region, such as by stabbing the seedling with one or more needles carrying the strain of *A. tumefaciens* to be tested. Alternatively, the tip of the seedling may be cut off, and the seedling then inoculated with the strain of *A. tumefaciens* to be tested. It is preferred to decapitate the seedling. The seedling is grown in a customary manner with periodic waterings and fertilization for a maximum of one year. The development of a grown gall at the site of inoculation identifies a strain of *A. tumefaciens* which is capable of transforming pine. Further details of this method will be described below.

The second assay method involves the inoculation of pine hypocotyls. In this method, pine seeds are nicked at the micropyle end and placed in hydrogen peroxide. After several days, the radical protrudes and the hypocotyl is about 3–5 cm long. The hypocotyl is then inoculated with a strain of *A. tumefaciens* to be tested. The inoculated hypocotyl is cultured. The development of gall on the hypocotyl identifies a strain of *A. tumerfaciens* which is capable of transforming pine. The gall can be removed and used to establish a callus. Further details of this method will be described below.

The present invention will be further described by reference to the following non-limiting examples.

EXAMPLE 1

Strains of *A. tumefaciens* were grown on potato dextrose agar plates. The plates were prepared by dissolving 39 g of potato dextrose agar obtained from either Gibco or Difco, and either 5 g or 10 g of $CaCO_3$ in one liter of distilled water.

*A. tumefaciens* was removed from the plate by a loop and suspended in L-broth for inoculation experiments. Two techniques were performed. First, two loopsful of *A. tumefaciens* were removed from the plate and suspended in 2 ml of L-broth. The bacteria was spun down at low speed for two minutes in an Eppendorf microcentrifuge Model 5413, and the pellet was resuspended in about 250 $\mu$l L-broth. This material was then used for inoculating pine cells. In the second method, one loopful or *A. tumefaciens* was removed from the plate and suspended in five drops of L-broth. This material was then used for inoculating pine cells.

EXAMPLE 2

Tests for opine synthesis are greatly simplified by knowledge of the type of opine produced by a given strain of *A. tumefaciens* because of the large number of different types of strain-specific opines.

The strain U3 was tested on sunflower, and was found to produce agropine and mannopine in gall-derived callus tissue. To test for the presence of these opines, between 20 and 40 $\mu$l of centrifuged supernate was spotted on electrophoretograms (Whatmann 3MM paper). Electrophoreses were conducted at 50 volts/cm under hydrocarbon coolant for 30–60 minutes at pH 1.8 (prepared from 2M acetic acid titrated with formic acid) and pH 4.0 (prepared from 0.1M acetic acid titrated with NaOH). Mannopine and agropine were routinely detected by dipping dried electrophoretograms in acetone containing 0.2% silver nitrate, drying at room temperature for 10 minutes, and then dipping in alcoholic NaOH (10 g/liter). Silver nitrate developed electrophoretograms were preserved by photographic fixer (Kodak Rapid Fix). Mannopine and agropine were also detected as white spots on a blue background by dipping the electrophoretogram in a solution of sodium periodate in acetone, drying at room temperature and redipping in a 0.1% solution of benzidine. Zweig, G. et al, Eds., *Handbook of Chromatography*, Vol. II, pp. 103–173. Standards of mannopine were prepared synthetically. The agropine standard was provided by Dr. Stephen Ferrand (Loyola University, Chicago).

The strain M2/73 was tested on sulflower and was found to produce nopaline in gall-derived callus tissue. To test for the presence of nopaline, electrophoreses at pH 1.8 and pH 4.0 were conducted as described above. Nopaline was routinely detected by dipping dried electrophoretograms in a pentacyanoaquoferriate-acetone (1:1) reagent. Zweig, G. et al, supra. Standards of nopaline and nopaline lactam were prepared synthetically.

EXAMPLE 3

Loblolly pine seedlings approximately 5 cm in height were inoculated with various strains of *A. tumefaciens* in the following manner. The material used for inoculation was prepared according to the second method of Example 1. The pine seedlings were inoculated after decapitation by stabbing several times with a bundle of insect pins which had been dipped in the inoculating broth. The wound was then wrapped for three days with parafilm to keep it moist. The parafilm was then removed. The seedlings were watered and fertilized at regular intervals while growing in a greenhouse with a photo period of 16 hours, and the wound sites examined for crown gall growth. Inoculation of pine seedlings with *A. tumefaciens* U3 resulted in crown gall growth. Inoculation with strains K27, C58, K289, A4, 35, 40, 41, W2/73, K9/73, K15/73, M2/73, S1/73, U11, C2/74, C3/74, CG-1CA, K6/73 and K224 did not produce crown galls. The crown gall was first seen after about two months and continued to grow for several additional months, resulting in galls several times the stem width of the seedling. The gall was sprayed with captan and malathion to reduce potential contamination. Galls were produced at about 3% efficiency.

EXAMPLE 4

The galls obtained in Example 3 were cut off the plant and surface-sterilized with 5% (w/v) calcium hypochlorite followed by extensive rinsing in distilled water. The surface of the gall was peeled away and the core was sliced into segments and placed on Litvay's medium (Litvay, J. D. et al, *Inst. Pap. Chem. Tech. Pap.* 115, 1 (1981)) with or without hormones.

The hormones which were included in the medium were 2 $\mu$M 6-benzylaminopurine and 2 $\mu$M $\alpha$-naphthalene acetic acid. Gall segments grew well in the presence of hormone and formed friable green callus.

Callus cultures of gall-derived tissue were propagated through several passages. Growth was markedly reduced if phytohormones were not added to the medium. Extracts of tissue were prepared by homogenization of cell masses in a glass Dounce-type homogenizer with two times the tissue weight of 80% ethanol. The resulting suspensions were spun in an Eppendorf microcentrifuge for 10 minutes. The ethanol-containing supernates were stored for opine analysis.

EXAMPLE 5

Loblolly pine hypocotyls were inoculated with various strains of *A. tumefaciens* in the following manner. The material used for inoculation was prepared according to the second method of Example 1. Hypocotyls from germinated seeds were prepared as follows. Pine seeds were nicked with a scalpel or razor blade at the micropyle end. The female gametophyte was barely nicked but the brown "paper" was cut. No more than 100 nicked seeds were placed in a 250 ml Erlenmeyer flask containing 100 ml of freshly prepared 1% $H_2O_2$. The flask was plugged with foam or cotton and placed in a warm place at about 28° C. to 30° C. The $H_2O_2$ was changed every day for 4–5 days. Alternatively, the $H_2O_2$ concentration was dropped to 0.03% after two days. The seeds were ready for inoculation when the radical protruded. In 4–5 days, the hypocotyls were about 3–5 cm long.

The seeds were then dissected and hypocotyls were inserted into tissue culture agar with one tip extending at least 5 mm out of the medium. The medium utilized for culturing the hypocotyls was one-half strength Gresshoff and Doy. Gresshoff, P. M. et al, Plants 107, 161 (1972). The tips of the hypocotyls were inoculated with bacteria from freshly grown plates as described in Example 3 and incubated for at least 60 days. About 2% of the hypocotyls showed localizaed swelling which resembled gall tissue, except that it was more succulent. The hypocotyls were then sliced in cross-sections and segments were cultured on medium containing phytohormones to produce callus as described in Example 4. After several passages, the callus was blotted dry and extracted with ethanol as described in Example 4 for opine analysis. All of the strains of *A. tumefaciens* tested in Example 2 were also tested by this method. Only strain M2/73 caused growth on the hypocotyl.

EXAMPLE 6

A gall obtained in Example 2 was cut off the plant and surface-sterilized with 5% (w/v) calcium hypochlorite followed by extensive rinsing in distilled water. Peelings from the gall (150 mg) were extracted with ethanol. The extract was analyzed for agropine and mannopine by electrophoresis at pH 1.8 as previously described, and gave a silver nitrate positive spot comigrating with the agropine standard and a weaker silver nitrate positive spot comigrating with the mannopine standard. The stronger spot also gave a positive test with sodium periodate-benzidine, characteristic of agropine. No such substances were present either in extracts of uninfected pine stems or in extracts of uninfected callus. The gall contained on the order of 20 $\mu$g agropine per gram fresh weight of gall segment and less mannopine as estimated by silver nitrate developed spot intensity.

The supernate prepared in Example 4 was analyzed as previously described. The supernate showed stronger silver nitrate positive spots that co-electrophoresed with the mannopine and agropine standards at pH 1.8. The extract contained about 500 $\mu$g of agropine per gram fresh weight of callus and about half that amount of mannopine.

The presence of agropine and mannopine were further confirmed by electrophresis. The agropine and mannopine in the extract were separately purified by preparative electrophoresis at pH 1.8 using 200 to 400 $\mu$l of extract. Appropriate bands were cut out and eluted with water to recover the purified opines. Each purified opine from the U3 callus tissue was electrophoresed side-by-side with authentic opine and in mixture with authentic opine. No distinction could be found between the faster migrating substance purified from the U3 tumor-derived callus and the agropine standard. Similarly, no difference could be found between the slower migrating substance and the mannopine standard.

EXAMPLE 7

The supernate prepared in Example 5 was analyzed for nopaline as previously described at pH 1.8 and 4.0. Both electrophoretograms showed phenanthrenequinone positive spots that comigrated with the nopaline and with nopaline lactam standards. Nopaline from the extract was purified by electrophoresis and compared with the nopaline standard on a long electrophoretic run. No difference was found between the purified opine and the nopaline standard. The nopaline content of the extract made with the callus was about 1 mg of nopaline per gram of blotted fresh weight and much less nopaline lactam, based on the phenanthrenequinone developed spot intensity.

While the invention has been described in connection with specific embodiments thereof, it will be understood that it is capable of further modification. This application is intended to cover any variations, uses or adaptations of the invention following, in general, the principles of the invention and including such departures from the present schedule as come within known and customary practice within the art to which the invention pertains.

What is claimed is:

1. A method for transforming pine, comprising inoculating differentiated pine tissue with a strain of *Agrobacterium tumefaciens* selected from the group consisting of (i) a strain containing a Ti plasmid which is capable of causing crown gall in said pine, (ii) a strain containing a plasmid comprising the vir region of said Ti plasmid and TDNA borders, and (iii) a strain containing a first plasmid comprising the vir region of said Ti plasmid and a second plasmid comprising TDNA borders.

2. The method of claim 1, wherein said pine is *Pinus taeda*.

3. The method of claim 1, wherein said differentiated pine tissue is selected from the group consisting of pine seedling tissue, pine hypocotyl tissue, and pine leaf tissue.

4. The method of claim 1, wherein said strain is selected from the group consisting of U3 and M2/73.

5. A transformed pine comprising differentiated pine tissue, said differentiated pine tissue comprising cells transformed by a strain of *Agrobacterium tumefaciens* selected from the group consisting of (i) a strain containing a Ti plasmid which is capable of causing crown gall in said pine, (ii) a strain containing a plasmid comprising the vir region of said Ti plasmid and TDNA borders, and (iii) a strain containing a first plasmid comprising the vir region of said Ti plasmid and a second plasmid comprising TDNA borders.

6. The transformed pine of claim 5, wherein said differentiated pine tissue is selected from the group consisting of pine seedling tissue, pine hypocotyl tissue, and pine leaf tissue.

7. The transformed pine of claim 5, wherein said strain is selected from the group consisting of U3 and M2/73.

8. The transformed pine of claim 5, wherein said pine is selected from the class consisting of Christmas tree varieties.

9. The transformed pine of claim 5, wherein said pine is *Pinus lambertiana*.

10. The transformed pine of claim 5, wherein said pine is *Pinus ponderosa*.

11. The transformed pine of claim 5, wherein said pine is *Pinus radiata*.

12. The transformed pine of claim 5, wherein said pine is Afghan pine.

13. The transformed pine of claim 5, wherein said pine is *Pinus sylvestris*.

14. The transformed pine of claim 5, wherein said pine is *Pinus strobus*.

15. The transformed pine of claim 5, wherein said pine is *Pinus virginiana*.

16. A transformed pine produced by the process of claim 1, 2, 3 or 4.

* * * * *